United States Patent
Roessler et al.

(10) Patent No.: US 6,903,231 B1
(45) Date of Patent: Jun. 7, 2005

(54) PROCESSES FOR PRODUCING ESTERS OF UNSATURATED CARBOXYLIC ACIDS AND POLYHYDRIC ALCOHOLS WITH LIMITED POLYMERIZATION, AND APPARATUS THEREFOR

(75) Inventors: Harald Roessler, Duesseldorf (DE); Matthias Fies, Krefeld (DE); Bernhard Gutsche, Hilden (DE); Theo Stalberg, Monheim (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 19 days.

(21) Appl. No.: 10/049,330
(22) PCT Filed: Aug. 3, 2000
(86) PCT No.: PCT/EP00/07496
§ 371 (c)(1), (2), (4) Date: Jun. 14, 2002
(87) PCT Pub. No.: WO01/12315
PCT Pub. Date: Feb. 22, 2001

(51) Int. Cl.$^7$ .............................. C07C 69/52
(52) U.S. Cl. .................. 560/224; 560/205; 560/206
(58) Field of Search ................. 560/129, 155, 560/205, 206

(56) References Cited

U.S. PATENT DOCUMENTS

| | | |
|---|---|---|
| 5,210,281 A | 5/1993 | Ritter et al. |
| 5,322,960 A * | 6/1994 | Sakamoto et al. .......... 560/205 |
| 5,648,518 A | 7/1997 | Ritter et al. |
| 5,883,288 A | 3/1999 | Iffland et al. |
| 6,506,930 B1 * | 1/2003 | Venter et al. .............. 560/205 |

FOREIGN PATENT DOCUMENTS

| | | |
|---|---|---|
| DE | 38 43 930 A1 | 6/1990 |
| DE | 38 43 843 A1 | 7/1990 |
| EP | 0 713 857 A1 | 5/1996 |
| EP | 0 850 954 A1 | 7/1998 |
| EP | 0 916 643 A1 | 5/1999 |

* cited by examiner

Primary Examiner—Johann Richter
Assistant Examiner—Karl Puttlitz
(74) Attorney, Agent, or Firm—Aaron R. Ettelman

(57) ABSTRACT

Processes and apparatus for producing esters are described. The processes include: (a) providing a liquid reaction mixture comprising (i) an unsaturated carboxylic acid having a boiling point greater than water, (ii) a polyhydric alcohol, and (iii) a first polymerization inhibitor, in a reaction zone having an inner surface; (b) reacting the acid and the polyhydric alcohol to form an ester, such that a gas/vapor phase is formed comprising water of reaction; (c) removing at least a portion of the gas/vapor phase from the reaction zone to a dephlegmation zone having an inner surface; (d) partially condensing the portion of the gas/vapor phase in the dephlegmation zone such that a condensate is formed; and (e) returning the condensate to the reaction zone; wherein a second polymerization inhibitor is introduced into the dephlegmation zone such that the portion of the gas/vapor phase and/or the condensate are contacted with the second polymerization inhibitor. Apparatus for carrying out the processes are also described.

21 Claims, 1 Drawing Sheet

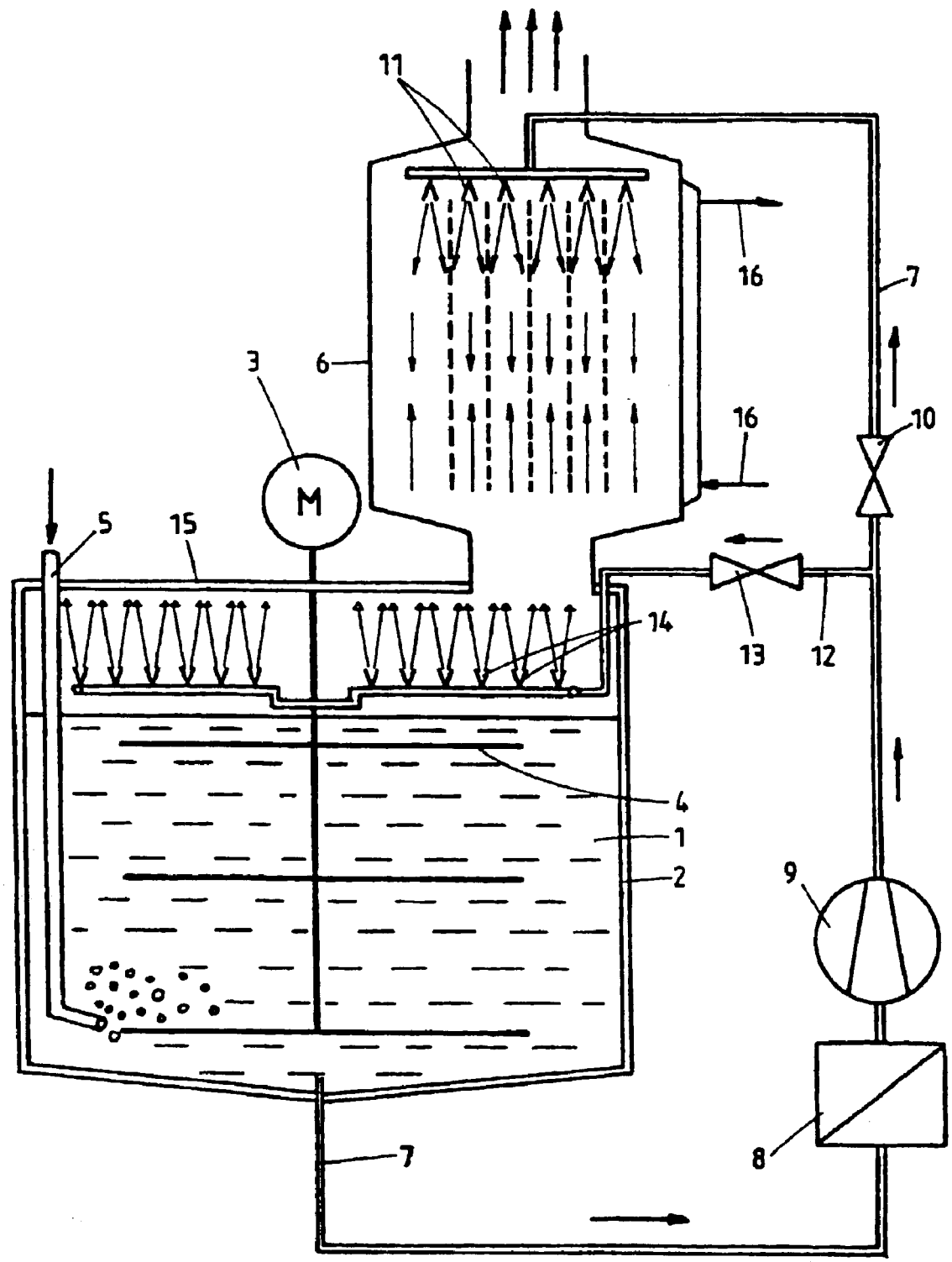

PROCESSES FOR PRODUCING ESTERS OF UNSATURATED CARBOXYLIC ACIDS AND POLYHYDRIC ALCOHOLS WITH LIMITED POLYMERIZATION, AND APPARATUS THEREFOR

BACKGROUND OF THE INVENTION (Meth)acrylic acid esters of polyhydric alcohols, more particularly from the group of dihydric to tetrahydric aliphatic saturated alcohols and alkoxylation products thereof, are being increasingly used as highly reactive constituents in radiation-curing systems. Polyfunctional (meth)acrylic acid esters may be used, for example, as paint raw materials for electron beam hardening or as a constituent of UV-hardening printing inks or corresponding coatings, surfacing, molding or potting compounds or even in adhesives, particularly anaerobically curing adhesives. However, their production is not without problems. There is a demand above all for colorless products with a low acid value and high storage stability which also have virtually no odor of their own. Purification of the (meth)acrylic acid esters in question here by distillation is generally not possible on account of their high molecular weight and their high reactivity. Accordingly, the products should be directly obtained as colorless esterification products. Carrying out of the esterification reactions involves the presence of highly effective inhibitors which, for their part, do not initiate any unwanted secondary reactions, for example in the form of discolorations. In addition, it can be desirable not only to protect the liquid reaction product from unwanted polymerization reactions during the esterification reaction, but also to ensure adequate inhibition of the entire reaction space including both the inner gas space and the wall surfaces which come into contact with the inner gas space. This counteracts the danger of unwanted polymer formation, for example on unprotected walls, the washing off of such polymers into the reaction product leading to an unwanted increase in the viscosity of the end product or to unwanted insoluble particles.

However, the invention is not confined to the production of (meth)acrylic acid esters, but instead relates to any esters of unsaturated carboxylic acids with a higher boiling point than water and polyhydric alcohols.

The above-described process is known, for example, for DE 3843843 A1. The reaction space is purged with an oxygen-containing gas stream and that part of the inner reaction space which is filled with the gas phase is charged with the fine droplets of liquid which contain the polymerization inhibitor. In this way, not only is the reactive liquid phase effectively stabilized by polymerization inhibitors, the entire inner reaction space is protected against unwanted polymerization reactions. The same inhibitor is used both for protecting the reactive liquid phase and for protecting the gas- or vapor-filled inner space and the solid surfaces (inner walls, stirrer components, etc.) arranged therein. In another process of the type mentioned at the beginning, the water of condensation formed during the reaction is removed from the gas phase of the reaction space. Finally, DE 3843930 A1 describes the polymerization inhibitors preferably used in the process mentioned at the beginning.

In the acid-catalyzed batch or semibatch esterification process, an inhibitor system which acts chemically in the liquid reaction mixture and which consists, for example, of a hydroquinone derivative in combination with atmospheric oxygen is used to prevent polymerization both of the unsaturated carboxylic acid used and of the unsaturated polyol ester formed. During the esterification, the water of reaction formed is removed from the reaction mixture by distillation under reduced pressure to obtain high conversion levels. With volatile unsaturated carboxylic acids, such as acrylic and methacrylic acid, a water/carboxylic acid mixture with a composition corresponding to the phase equilbrium is removed from the circuit. This known process has two major disadvantages when used for the esterification of volatile unsaturated carboxylic acids:

First, the removal of water/carboxylic acid from the circuit inevitably leads to a large stoichiometric excess of carboxylic acid, based on the polyol used, which can amount to between 40 and 50% in the case of tri- and tetrahydric polyols.

Second, the hydroquinone/air system—which only has an inhibiting effect in the liquid reaction mixture—is attended by the danger that the noninhibited unsaturated carboxylic acid present in the gas phase during the removal of water from the circuit polymerizes during the condensation, leading to serious problems in the process.

Accordingly, the problem addressed by the present invention was significantly to reduce the excess of carboxylic acid in the process mentioned at the beginning and to prevent the polymerization of carboxylic acid or ester in the liquid or gas phase. In addition, the reaction time would be shortened and the level of organic pollutants in the wastewater wold be reduced.

BRIEF SUMMARY OF THE INVENTION

Accordingly, the present invention relates to a process for the production of esters of unsaturated carboxylic acids with a higher boiling point than water, more particularly acrylic acid or methacrylic acid, and polyhydric alcohols in a reactor, the liquid reaction mixture containing polymerization inhibitors and the water of reaction formed being at least partly removed in vaporous form, characterized in that part of the gas/vapour phase of the reaction mixture is removed from the reactor and is partly condensed in a dephlegmator, a liquid containing the polymerization inhibitor is introduced into the ascending gas/vapor mixture and the descending condensate from the head of the dephlegmator and the entire outflowing mixture is returned to the reactor.

In the condensate which is enriched with carboxylic acid, polymerization is prevented by addition of the inhibitor so that the condensate can readily be returned to the reaction mixture. This recycling enables the carboxylic acid excess required for the reaction to be reduced from 20–40% in the known process to 5–10. The partial condensation of the unsaturated carboxylic acid leads to a vapor phase distinctly enriched with water and hence to faster distillation and a shorter reaction time. After removal from the circuit, the water-enriched vapor phase is condensed, the condensate being disposed of as wastewater. In contrast to the prior art, this wastewater contains a far lower percentage of unsaturated carboxylic acids and, accordingly, has a far lower level of organic pollutants.

BRIEF DESCRIPTION OF THE SEVERAL VIEWS OF THE DRAWING

The drawing shows a general diagram of the apparatus according a preferred embodiment of the invention.

DETAILED DESCRIPTION OF THE INVENTION

According to the invention, an external inhibitor solution may be added to the condensate enriched with carboxylic acid. In one particularly advantageous embodiment, however, part of the liquid reaction mixture is branched off for this purpose and is added to the ascending gas/vapor mixture and to the descending condensate. Part of the liquid reaction mixture is thus circulated.

The above-mentioned cooling of the gas/vapor phase of the reaction mixture removed from the circuit can be effected by spraying a comparatively cold liquid containing the inhibitor—more particularly the reaction mixture—into the vapor pipe. It has been found to be possible in this way, i.e. without using a dephlegmator, both to separate carboxylic acid and water and to prevent polymerization of the condensated carboxylic acid.

In a preferred embodiment, however, the gas/vapor mixture removed from the reaction mixture can be partly condensed in a dephlegmator, a liquid phase enriched with carboxylic acid running off and a water-rich vapor phase leaving the dephlegmator and wetting its inner walls with the liquid containing the polymerization inhibitor. Particularly effective separation of water and carboxylic acid is achieved through the use of the dephlegmator. In one particular embodiment, a vertical tube-bundle heat exchanger of stainless steel is used as the dephlegmator. By spraying the inner walls of the dephlegmator, inhibition is achieved immediately after condensation of the carboxylic acid.

It has also been found that the separation of carboxylic acid and water is further improved if the liquid containing the polymerization inhibitor has a temperature below or at most up to the reaction temperature. Accordingly, after part of the reaction mixture has been branched off, this part is preferably cooled before it is sprayed onto the inner walls of the dephlegmator.

In order to ensure that the condensed mixture enriched with unsaturated carboxylic acid which flows back into the reactor does not under any circumstances polymerize on the inside of the reactor cover or on internals in the upper interior of the reactor, for example on parts of the stirrer, the condensate is returned to the reactor from above and a liquid containing the polymerization inhibitor, more particularly a part branched off from the liquid reaction mixture, is fed to and more particularly sprayed onto the inner walls and internals in the upper part of the reactor, more particularly the inner wall of the reactor cover. In this way, the tendency of the condensate to polymerize on the parts mentioned is effectively prevented.

The present invention also relates to an installation for carrying out the described process comprising a reactor surmounted by a vapor pipe for removing water from the reaction mixture.

In this case, the above-stated problem addressed by the invention is solved by a first pipe extending from the lower part of the reactor to the vapor pipe, first spray nozzles arranged within the vapor pipe at the outlet of the first pipe, the spray nozzles being directed in particular oppositely to the ascending vapors, and a pump in the first pipe.

In a particularly preferred embodiment, the vapor pipe is in the form of a dephlegmator surmounting the reactor and the first spray nozzles are directed onto the inner walls of the dephlegmator.

In addition, in order further to improve the separation of water and carboxylic acid in the condensate, a cooler in the first pipe is of advantage.

In order to prevent polymerizations in the upper inner part of the reactor, a second pipe—either extending from the lower part of the reactor or branched off from the first pipe—is provided and second spray nozzles are arranged at the outlet of the second pipe and are directed onto the inner walls and internals in the upper part of the reactor, more particularly onto the inner wall of the reactor cover.

One example of embodiment of the installation according to the invention is described in detail in the following with reference to the accompanying drawing (FIG. 1) which schematically illustrates the plant.

The liquid reaction mixture 1 in the heated reactor 2 is mixed by a stirrer 4 driven by a motor 3. The reaction mixture 1 contains the polymerization inhibitor, the unsaturated carboxylic acid, the polyhydric alcohol and the secondary reaction product, water, and the reaction product, the ester. Air is injected into the reaction mixture 1 from below through a pipe 5.

The vapor phase above the liquid reaction mixture 1 is removed under reduced pressure through a dephlegmator 6 fitted onto the reactor 2. The dephlegmator is a vertical tube-bundle heat exchanger of which the inner walls are indicated by chain lines. After removal of most of the carboxylic acid, the water-enriched vapor phase is removed upwards and liquefied in a condenser (not shown). The water containing only a relatively small amount of carboxylic acids is disposed of as wastewater. The dephlegmator 6 is cooled with water through pipes 16.

From the bottom of the reactor 2, a first pipe 7 leads via a filter 8, which retains a polymerized fractions, a pump 9 and a valve 10 to first spray nozzles 11 in the upper part of the dephlegmator 6. The first spray nozzles 11 are directed downwards onto the inner walls of the dephlegmator 6.

Branching off from the first pipe 7 is a second pipe 12 through which the reaction mixture 1 passes via a valve 13 to second spray nozzles 14 which are arranged in the upper part of the reactor 2 above the liquid surface and which are directed upwards onto the inner wall of the reactor cover 15.

The installation operates as follows:

Water/carboxylic acid vapors ascend from the liquid heated reaction mixture into the dephlegmator 6. At the same time, the inhibited liquid reaction mixture flows in countercurrent down the inner walls of the dephlegmator 6 and—similarly to a rectifying column operated under reflux—intensities the separation of carboxylic acid and water. In addition, the condensed unsaturated carboxylic acids are prevented from polymerizing on the walls of the dephlegmator.

In the upper part of the inner reactor space, the inhibited reaction mixture is sprayed by the second spray nozzles 14 arranged on a nozzle ring onto the inner wall of the reactor cover 15 and onto the noninhibited carboxylic acid flowing down the reactor cover from the dephlegmator 6. Polymerization in the cover region of the reactor is prevented in this way.

A vertical tube-bundle reactor with a liquid inlet at its head via the first spray nozzles 11 is used as the dephlegmator 6. The ratio of tube diameter to tube length is at least 0.03:1. The heat exchanger has an exchange area of at least 10 $m^2$ per $m^3$ reactor volume.

What is claimed is:

1. A process for producing esters, said process comprising:

(a) providing a liquid reaction mixture comprising (i) an unsaturated carboxylic acid having a boiling point greater than water, (ii) a polyhydric alcohol, and (iii) a first polymerization inhibitor, in a reaction zone having an inner surface;

(b) reacting the acid and the polyhydric alcohol to form an ester, such that a gas/vapor phase is formed comprising water of reaction;

(c) removing at least a portion of the gas/vapor phase from the reaction zone to a dephlegmation zone having an inner surface;

(d) partially condensing the portion of the gas/vapor phase in the dephlegmation zone such that a condensate is formed; and (e) returning the condensate to the reaction zone;

wherein a second polymerization inhibitor is introduced into the dephlegmation zone such that the portion of the gas/vapor phase and/or the condensate are contacted with the second polymerization inhibitor.

2. The process according to claim 1, wherein the second polymerization inhibitor and the first polymerization inhibitor are the same.

3. The process according to claim 1, wherein the second polymerization inhibitor introduced into the dephlegmation zone comprises a portion of the liquid reaction mixture which is removed from the reaction zone.

4. The process according to claim 1, wherein the inner surface of the dephlegmation zone is wetted with a mixture of the condensate and the second polymerization inhibitor.

5. The process according to claim 1, wherein the second polymerization inhibitor is introduced into the dephlegmation zone at a temperature below the reaction temperature.

6. The process according to claim 1, wherein a third polymerization inhibitor is introduced into the reaction zone such that a portion of the inner surface of the reaction zone which is not in contact with the reaction mixture is contacted with the third polymerization inhibitor.

7. The process according to claim 3, wherein a third polymerization inhibitor is introduced into the reaction zone such that a portion of the inner surface of the reaction zone which is not in contact with the reaction mixture is contacted with the third polymerization inhibitor.

8. The process according to claim 6, wherein the third polymerization inhibitor and the first polymerization inhibitor are the same.

9. The process according to claim 6, wherein the second polymerization inhibitor, the third polymerization inhibitor and the first polymerization inhibitor are the same.

10. The process according to claim 7, wherein the second polymerization inhibitor, the third polymerization inhibitor and the first polymerization inhibitor are the same.

11. The process according to claim 6, wherein the third polymerization inhibitor introduced into the reaction zone comprises a portion of the liquid reaction mixture which is removed from the reaction zone.

12. The process according to claim 7, wherein the third polymerization inhibitor introduced into the reaction zone comprises a portion of the liquid reaction mixture which is removed from the reaction zone.

13. The process according to claim 6, wherein the third polymerization inhibitor is introduced into the reaction zone at a temperature below the reaction temperature.

14. The process according to claim 1, wherein air is injected into the reaction mixture during the reaction.

15. The process according to claim 1, wherein the removal of the portion of the gas/vapor phase from the reaction zone to a dephlegmation zone is carried out under reduced pressure.

16. The process according to claim 1, wherein the dephlegmation zone comprises a dephlegmator attached to the top of the reaction zone.

17. The process according to claim 1, wherein the dephlegmation zone comprises a vertical tube-bundle heat exchanger.

18. The process according to claim 1, wherein the second polymerization inhibitor is introduced into the dephlegmation zone via one or more spray nozzles.

19. The process according to claim 6, wherein the third polymerization inhibitor is introduced into the reaction zone via one or more spray nozzles.

20. The process according to claim 1, wherein the unsaturated carboxylic acid comprises a component selected from the group consisting of acrylic acid, methacrylic acid and mixtures thereof.

21. A process for producing esters, said process comprising:

(a) providing a liquid reaction mixture comprising (i) an unsaturated carboxylic acid selected from the group consisting of acrylic acid, methacrylic acid and mixtures thereof, (ii) a polyhydric alcohol, and (iii) a polymerization inhibitor, in a reaction zone having an inner surface;

(b) reacting the acid and the polyhydric alcohol to form an ester, such that a gas/vapor phase is formed comprising water of reaction;

(c) removing at least a portion of the gas/vapor phase from the reaction zone to a dephlegmation zone having an inner surface, under reduced pressure; and (d) partially condensing the portion of the gas/vapor phase in the dephlegmation zone such that a condensate is formed; and (e) returning the condensate to the reaction zone;

wherein a portion of the liquid reaction mixture is removed from the reaction zone and introduced into the dephlegmation zone such that the portion of the gas/vapor phase and the condensate are contacted with the portion of the liquid reaction mixture and the inner surface of the dephlegmation zone is wetted with a mixture of the condensate and the portion of the liquid reaction mixture; and wherein a second portion of the liquid reaction mixture is removed from the reaction zone and reintroduced into the reaction zone such that a portion of the inner surface of the reaction zone which is not in contact with the reaction mixture is contacted with the second portion of the liquid reaction mixture.

* * * * *